(12) United States Patent
Deladi et al.

(10) Patent No.: US 10,792,099 B2
(45) Date of Patent: Oct. 6, 2020

(54) ENERGY APPLICATION APPARATUS FOR APPLYING ENERGY TO AN OBJECT

(75) Inventors: Szabolcs Deladi, Veldhoven (NL); Godefridus Antonius Harks, Rijen (NL); Gerardus Henricus Maria Gijsbers, Liempde (NL); Jan Frederik Suijver, Dommelen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 489 days.

(21) Appl. No.: 13/704,005

(22) PCT Filed: Jun. 24, 2011

(86) PCT No.: PCT/IB2011/052771
§ 371 (c)(1),
(2), (4) Date: Feb. 4, 2013

(87) PCT Pub. No.: WO2012/001595
PCT Pub. Date: Jan. 5, 2012

(65) Prior Publication Data
US 2013/0158537 A1      Jun. 20, 2013

(30) Foreign Application Priority Data

Jun. 30, 2010   (EP) .................................... 10167804

(51) Int. Cl.
*A61B 18/18* (2006.01)
*A61B 18/12* (2006.01)
(Continued)

(52) U.S. Cl.
CPC .......... *A61B 18/18* (2013.01); *A61B 18/1492* (2013.01); *A61B 34/20* (2016.02);
(Continued)

(58) Field of Classification Search
CPC .......... A61B 18/14; A61M 25/10; A61N 1/40; A61N 1/06; A61N 1/08; A61N 1/05
(Continued)

(56) References Cited

U.S. PATENT DOCUMENTS

| 6,315,776 | B1 | 11/2001 | Edwards et al. |
| 6,824,515 | B2 | 11/2004 | Suorsa et al. |

(Continued)

FOREIGN PATENT DOCUMENTS

| WO | WO2009032421 | 3/2009 |
| WO | WO2009090588 | 7/2009 |
| WO | WO2010009473 | 1/2010 |

OTHER PUBLICATIONS

D.J. Sahn, et al., "A Family of Intracardiac Ultrasound Imaging Devices Designed for Guidance of Electrophysiology Ablation Procedures", 31st Annual international Conference of the IEEE EMBS Minneapolis, MN, USA, Sep. 2-6, 2009, pp. 1913-1917.

*Primary Examiner* — Jon Eric C Morales

(57) ABSTRACT

The invention relates to an energy application apparatus for applying energy to an object. A plurality of energy application elements (4) applies energy to the object at different locations and at least one ultrasound element (18) generates an ultrasound signal being indicative of a property of the object at the different locations, wherein at least one energy application element is individually controlled depending on an energy application influence, in particular, an ablation depth, determined for the location at which the at least one energy application element applies energy from the ultrasound signal. Thus, at least one local control point for applying energy to the object is provided, thereby improving the control of applying energy to the object.

13 Claims, 10 Drawing Sheets

(51) Int. Cl.
  *A61B 18/14* (2006.01)
  *A61B 18/00* (2006.01)
  *A61B 17/00* (2006.01)
  *A61B 90/00* (2016.01)
  *A61B 34/20* (2016.01)

(52) U.S. Cl.
  CPC ..... *A61B 90/37* (2016.02); *A61B 2017/00106* (2013.01); *A61B 2018/00029* (2013.01); *A61B 2018/0088* (2013.01); *A61B 2018/00214* (2013.01); *A61B 2018/00577* (2013.01); *A61B 2018/00654* (2013.01); *A61B 2018/00982* (2013.01); *A61B 2090/374* (2016.02); *A61B 2090/376* (2016.02); *A61B 2090/378* (2016.02); *A61B 2090/3764* (2016.02)

(58) Field of Classification Search
  USPC .............................................. 606/41; 607/105
  See application file for complete search history.

(56) References Cited

U.S. PATENT DOCUMENTS

| | | | |
|---|---|---|---|
| 7,494,467 | B2 | 2/2009 | Makin et al. |
| 8,702,609 | B2 | 4/2014 | Hadjicostis |
| 2003/0153907 | A1* | 8/2003 | Suorsa ............... A61B 18/1492 606/41 |
| 2005/0283074 | A1 | 12/2005 | Jackson et al. |
| 2007/0005053 | A1 | 1/2007 | Dando |
| 2007/0156048 | A1 | 7/2007 | Panescu et al. |
| 2008/0146918 | A1* | 6/2008 | Magnin ............... A61B 8/0841 600/437 |
| 2009/0036914 | A1 | 2/2009 | Houser |
| 2012/0004547 | A1* | 1/2012 | Harks ................. A61B 8/0858 600/439 |
| 2012/0105480 | A1* | 5/2012 | Barley ................. A61B 90/36 345/641 |
| 2014/0180101 | A1 | 6/2014 | Hadjicostis |

\* cited by examiner

ENERGY APPLICATION APPARATUS FOR APPLYING ENERGY TO AN OBJECT

FIELD OF THE INVENTION

The invention relates to an energy application apparatus, energy application method and energy application computer program for applying energy to an object. The invention relates further to a catheter for being introduced into the object and a controller for controlling the application of energy to the object.

BACKGROUND OF THE INVENTION

US 2007/0156048 A1 discloses a medical catheter comprising a flexible elongate body having a proximal end and a distal end. A plurality of spaced apart electrodes is operably attached to the flexible body near the distal end, wherein at least one of the electrodes is adapted for ablating a desired portion of the tissue and wherein a plurality of ultrasound transducer elements is provided interspaced amongst the electrodes. The ultrasound transducer elements produce ultrasound signals which are used for determining whether the ultrasound transducer elements are in contact with the tissue. If an ultrasound transducer element is in contact, the tissue is ablated via an electrode being adjacent to the ultrasound transducer element.

If the medical catheter is used for applying energy to cardiac tissue, the cardiac tissue may be overheated at the ablation site. This can lead to, for example, rupturing of the cardiac tissue at the ablation site and/or to a damage of neighboring organs and tissues. The cardiac tissue can also be undertreated at the ablation site. In this case, after the person has recovered from the ablation procedure, a second ablation procedure may be needed. Besides the costs and risks involved with the second ablation procedure, a repeated ablation procedure is generally more difficult for the therapist because of scar tissue present from the first ablation procedure.

SUMMARY OF THE INVENTION

It is an object of the present invention to provide an energy application apparatus, energy application method and energy application computer program for applying energy to an object, wherein the control of applying energy to an object can be improved. In a first aspect of the present invention an energy application apparatus for applying energy to an object is presented, wherein the energy application apparatus comprises:
  a plurality of energy application elements for applying energy to the object at different locations,
  at least one ultrasound element for generating an ultrasound signal being indicative of a property of the object at the different locations,
  an energy application influence determining unit for determining an energy application influence of the applied energy to the different locations from the generated ultrasound signal,
  a control unit for individually controlling at least one energy application element depending on the energy application influence determined for the location at which the at least one energy application element applies energy. Thus, the energy application elements and the control unit are preferentially adapted to individually control the energy application elements depending on the energy application influence determined for the location at which the respective energy application element applies energy.

Since the energy application influence determining unit determines an energy application influence of the applied energy to the different locations from the generated ultrasound signal and since at least one energy application element is individually controlled depending on the energy application influence determined for the location to which the at least one energy application element applies energy, i.e. since at least one local control point for applying energy to the object is provided, the control of applying energy to the object is improved. This can lead to a safer and more efficient application of energy.

The property at the different locations can be sensed directly, i.e. by directing ultrasound waves directly to the different locations to which energy is applied, or indirectly, i.e. by directing the ultrasound waves to adjacent regions being adjacent to the different locations, wherein the adjacent regions are also affected by the application of the energy to the different locations. Thus, a property of the object at a certain location can be sensed by directing ultrasound waves to a region being adjacent to the certain location. The energy application influence determining unit can be adapted to determine the energy application influence of the applied energy to the different locations from the ultrasound signal which has directly sensed the respective location or from an ultrasound signal which has indirectly sensed the respective location.

The at least one ultrasound element is preferentially an ultrasound transducer.

The control unit can be adapted to control the time, at which power is applied, the duration of applying power, and/or the level of power, in order to control the application of energy to a respective location, depending on the energy application influence determined for the respective location. The control unit can also be adapted to individually control one energy application element, a pair of energy application elements or a group comprising more than two energy application elements, which apply energy to the same location. Preferentially, single energy application elements can individually be controlled depending on the energy application influence determined for the location at which the respective individual energy application element applies energy.

It is preferred that the energy application apparatus comprises a plurality of ultrasound elements assigned to the plurality of energy application elements, wherein the control unit is adapted to control a respective energy application element depending on one or several energy application influences determined from one or several ultrasound signals of one or several ultrasound elements assigned to the respective energy application element. In particular, to each energy application element one or more ultrasound elements can be assigned, wherein the control unit is adapted to control a respective energy application element depending on the energy application influences determined from the ultrasound signals of the one or more ultrasound elements assigned to the respective energy application element. In an embodiment, several energy application elements, for example, a pair of energy application elements, can be assigned to the same one or several ultrasound elements, wherein the control unit is adapted to control the several energy application elements depending on the energy application influences determined from the ultrasound signals of the same one or several ultrasound elements.

It is further preferred that the energy application elements are ablation electrodes for creating a lesion line. The lesion line can be a line having an open or closed shape. For example, the lesion line can be a straight or a circular line. The ablation electrodes can be arranged along an annual ring which can be pressed towards, for instance, the ostium of the pulmonary veins, for generating a closed lesion line. In this example, the ablation electrodes are preferentially directed to the same ablation side of the energy application apparatus, which is pressed against the ostium of pulmonary veins. The control unit is preferably adapted to control the electrical energy of the ablation electrodes by controlling the time, at which power is applied, the duration of applying the power, and/or the level of the applied power. The ablation electrodes are preferentially adapted to perform a radiofrequency (RF) ablation procedure. The energy application elements can also be adapted to apply another kind of energy to the object like optical energy, coldness, et cetera. If the energy application elements are adapted to apply optical energy to the object, the energy application elements are preferentially optical fibers for applying, for example, laser light to the object. The energy application elements are preferentially adapted to perform an ablation procedure within a heart or another organ of a person or of an animal. However, the energy application elements can also be adapted to apply energy to another object like a technical object.

It is further preferred that the energy application apparatus comprises a catheter for introducing the plurality of energy application elements and the at least one ultrasound element into the object. For introducing the energy application elements and the at least one ultrasound element into the object, they are preferentially located within the catheter. The catheter is preferentially a heart catheter for introducing the plurality of energy application elements and the least one ultrasound element into the heart of a person or of an animal and for performing an ablation procedure within the heart.

It is further preferred that the catheter comprises at least one irrigation opening for allowing irrigation fluid to leave the catheter, wherein the at least one ultrasound element is arranged within the catheter such that the property of the object is sensible through the at least one irrigation opening. In particular, the catheter can comprise several irrigation openings and several ultrasound elements, wherein each ultrasound element can be arranged such that the property of the object is sensible, i.e. can be sensed, through the irrigation openings.

It is further preferred that the energy application influence determining unit is adapted to determine an ablation depth as the energy application influence from the ultrasound signal. In particular, energy application elements can be individually controlled depending on the development of a lesion, which is defined by the ablation depth and caused by the respective energy application element. Thus, local lesion progression can be determined and an energy application element can be controlled based on the determined local lesion progression.

In an embodiment, the ultrasound signal represents ultrasound reflection properties of the object at different depths, wherein the energy application influence determination unit is adapted to determine a discontinuity of the ultrasound signal and to determine the ablation depth as the depth of the ultrasound signal at which the discontinuity occurs. The ultrasound signal preferably also represents the ultrasound reflection properties at different times, thereby allowing determining the ablation depth at different times, in particular, in real-time. This allows controlling individual energy application elements in real-time depending on the local ablation depth, in particular, such that an overtreatment like an overheating and an undertreatment are prevented.

The energy application influence determination unit can be adapted to correct the ultrasound signal for a thermal expansion of the object caused by the ablation procedure and to determine the ablation depth and an ablation time as the depth and the time of temporally subsequent signal values of the corrected ultrasound signal, which correspond to the same depth and which are not similar with respect to a predefined similarity measure. The energy application influence determination unit can also be adapted to:

correct the ultrasound signal for a thermal expansion of the object caused by the ablation procedure, determine stretches comprised of temporally subsequent signal values of the corrected ultrasound signal, which correspond to the same depth and which are similar with respect to a similarity measure, determine the ablation depth and an ablation time as the depth and the time at which the length of the stretches is below a predefined threshold. This predefined threshold can be determined by a calibration measurement, wherein ultrasound signals are generated by sending ultrasound pulses into the object having a known ablation depth. In an embodiment, stretches having a length larger than 0.25 s, further preferred larger than 0.5 s and even further preferred larger than 1 s, are regarded as indicating that an ablation has not yet occurred at the respective depth.

In an embodiment, the energy application influence determination unit is adapted to:

correct the ultrasound signal for a thermal expansion of the object caused by the ablation procedure, determine, for different depth regions and at the different times, a cross correlation of temporally subsequent signal values of the same depth region, determine an ablation depth and an ablation time depending on the cross correlation of the temporally subsequent signals determined for the different depth regions and at the different times. In particular, the energy application influence determination unit is adapted to determine, for different depth regions and at the different times, a shift value depending on the determined cross correlation and to determine an ablation depth and an ablation time depending on the determined shift values, wherein a shift value is indicative of a shift between temporally subsequent signals within a depth region.

The ultrasound signal representing ultrasound reflection properties of the object at different depths and at different times is preferentially an M-mode image.

The cross correlation is preferentially performed in the Fourier domain, i.e. preferentially before determining the cross correlation the ultrasound signal is Fourier transformed, and after the cross correlation has been determined and before the shift values are determined an inverse Fourier transformation is preferentially performed. This performing of the cross correlation in the Fourier domain results in faster processing.

Preferentially, the depth dimension is subdivided into different depth regions, wherein for each depth region each line of signal values defined by the same time is cross correlated with its temporally preceding line of signal values which belong to the same preceding time. Thus, for the respective depth region a number of cross correlation lines is determined. The cross correlation lines of the respective depth region are preferentially averaged. This averaging is preferentially performed by applying an average filter to the cross correlation lines of the respective depth region.

The shift value at a depth region and at a time is preferentially determined by determining a peak of the cross correlation line of the respective depth region at the respective time. The depth position of the respective peak within the respective depth region is indicative of the shift between the two lines of signal values within the depth region, which have been cross correlated for determining the cross correlation line. The shift value is therefore preferentially determined from the depth position of the peak within the respective depth region. The accuracy of determining the depth position of the peak within the respective depth region is preferentially improved by fitting a parabola to the peak, wherein the maximum of the parabola is used as the depth position of the peak within the depth region. Preferentially, the peak is cut out of the respective cross correlation line before performing the fitting procedure, in order to fit the parabola to the peak only and not to the respective complete cross correlation line within the respective depth region.

For determining the ablation depth and the ablation time a thresholding is preferentially performed on the determined shift values. In an embodiment, if a shift value is larger than a predefined shift threshold, the corresponding depth region and time are preferentially regarded as ablation depth, at which the ablation process occurs, and as ablation time. A zone where tissue is coagulating corresponds to a region of poor cross correlation, i.e. corresponds to a region of a relatively large shift value. A healthy tissue zone and a zone including tissue that is already completely coagulated correspond to regions of good cross correlation, i.e. correspond to regions of a relatively small shift value. The zone at which tissue is actually coagulating can therefore be separated from a healthy tissue zone and a zone comprising tissue that is already completely coagulated by using the predefined shift threshold. This shift threshold can be predefined by, for example, calibration.

It is further preferred that the energy application apparatus further comprises an object wall thickness determining unit for determining an object wall thickness at the location at which the at least one energy application element applies energy from the ultrasound signal, wherein the control unit is adapted to control the at least one energy application element depending on the determined object wall thickness. In particular, energy application elements can be individually controlled depending on the development of a lesion caused by the respective energy application element and on the local object wall thickness. For example, the energy application elements can be controlled such that at desired ablation sites the generated lesion is transmural by controlling the energy application elements depending on the local ablation depth and the local object wall thickness.

The energy application apparatus preferentially comprises a plurality of ultrasound elements, wherein the energy application elements and the ultrasound elements can be alternately arranged. It is further preferred that the energy application apparatus comprises a plurality of ultrasound elements, which are integrated in the energy application elements. Preferentially, in each energy application element an ultrasound element is integrated. It is further preferred that the ultrasound elements are placed on an outer surface of the energy application elements. In particular, on the outer surface of each of the energy application elements an ultrasound element can be placed. It is further preferred that the energy application elements comprises an outer surface with an opening, which can be an irrigation opening, wherein the ultrasound elements are located within the energy application elements such that the property of the object can be sensed through the opening. Preferentially, several combinations of an energy application element and an ultrasound element are provided, wherein the ultrasound element of a combination is arranged within the respective energy application element such that the property of the object can be sensed through the opening in the outer surface of the energy application element. Since the ultrasound elements and the energy application elements are integrated, a location to which energy is applied by using a certain energy application element can easily be sensed by using the ultrasound element which is integrated in the certain energy application element.

If the energy application elements comprise an outer surface with an irrigation opening, wherein the ultrasound elements are located within the energy application elements such that the property of the object can be sensed through the respective irrigation opening, the property of the object at the locations at which energy is applied can easily and preferentially continuously be sensed by using the ultrasound elements, wherein the property of the object can be sensed before, during and/or after the application of energy. Through the irrigation opening irrigation fluid can leave the catheter, wherein the irrigation fluid can be used for cooling purposes and/or for irrigation purposes. The cooling of, for example, a lesion can be used for controlling the lesion quality. Moreover, the irrigation fluid can be used as mediating agent for providing a contact between the ultrasound elements and the object.

In a further aspect of the present invention a catheter for being introduced into an object is presented, wherein the catheter comprises:

a plurality of energy application elements for applying energy to the object at different locations, at least one ultrasound element for generating an ultrasound signal being indicative of a property of the object at the different locations, wherein the catheter is adapted to cooperate with:

an energy application influence determining unit for determining an energy application influence of the applied energy to the different locations from the generated ultrasound signal, a control unit for individually controlling at least one energy application element depending on the energy application influence determined for the location at which the at least one energy application element applies energy.

In further aspect of the present invention a controller for controlling the application of energy to an object is presented, wherein the controller is adapted to cooperate with:

a plurality of energy application elements for applying energy to the object at different locations, at least one ultrasound element for generating an ultrasound signal being indicative of a property of the object at the different locations, wherein the controller comprises:

an energy application influence determining unit for determining an energy application influence of the applied energy to the different locations from the generated ultrasound signal, a control unit for individually controlling at least one energy application element depending on the energy application influence determined for the location at which the at least one energy application element applies energy.

In a further aspect of the present invention an energy application method for applying energy to an object is presented, wherein the energy application method comprises:

applying energy to the object at different locations by a plurality of energy application elements, generating an ultrasound signal being indicative of a property of the object at the different locations by at least one ultrasound element, determining an energy application influence of the applied energy to the different locations from the generated ultrasound signal by an energy application influence determining unit, individually controlling at least one energy application element depending on the energy application influence determined for the location at which the at least one energy application element applies energy by a control unit.

In a further aspect of the present invention a computer program for applying energy to an object is presented, wherein the computer program comprises program code means for causing an energy application apparatus as defined in claim 1 to carry out the steps of the energy application method as defined in claim 14, when the computer program is run on a computer controlling the energy application method.

It shall be understood that the energy application apparatus of claim 1, the catheter of claim 12, the controller of claim 13, the energy application method of claim 14 and the computer program of claim 15 have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
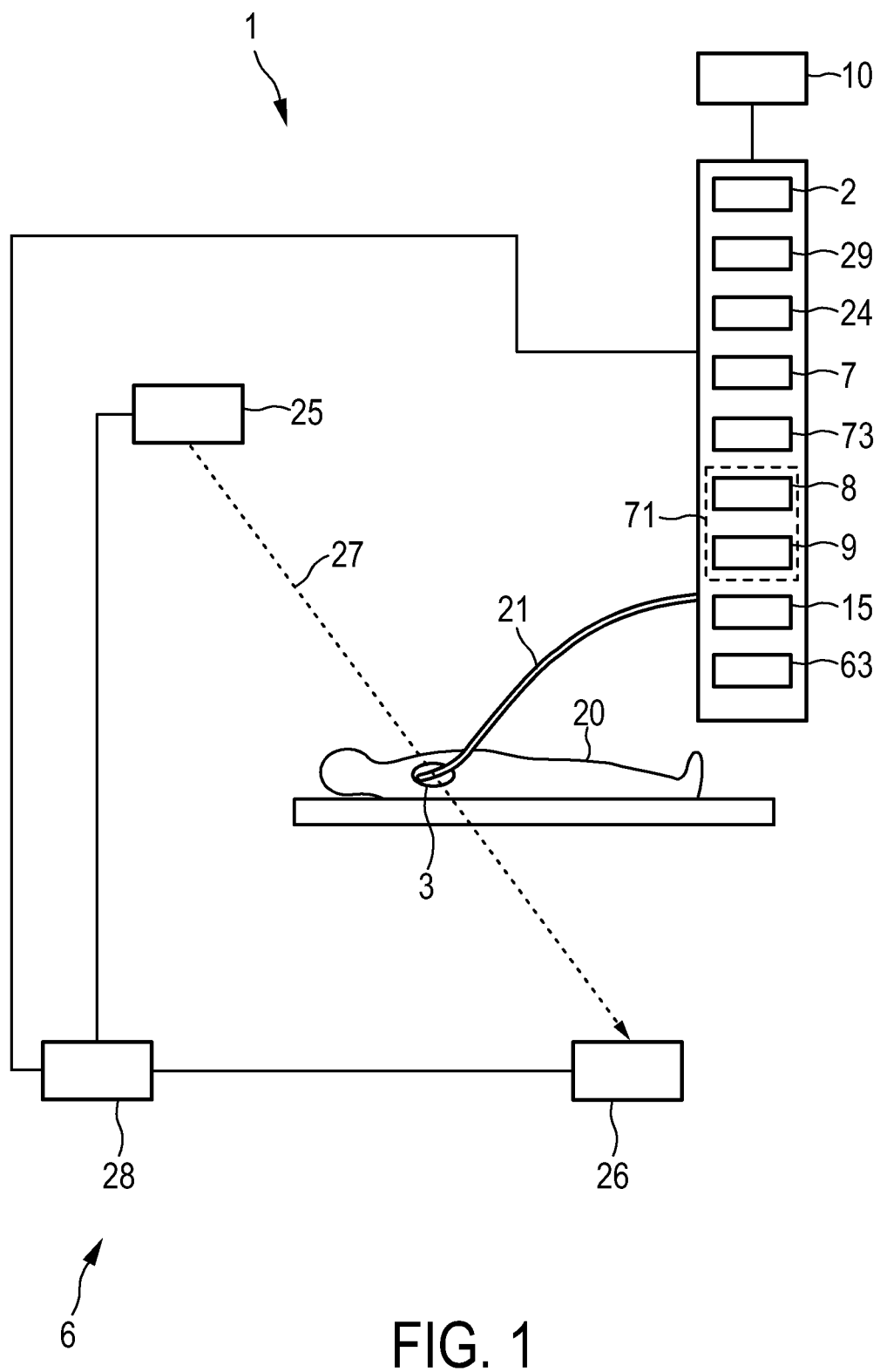
FIG. 1 shows schematically and exemplarily an energy application apparatus for applying energy to an object.
Figure 2:
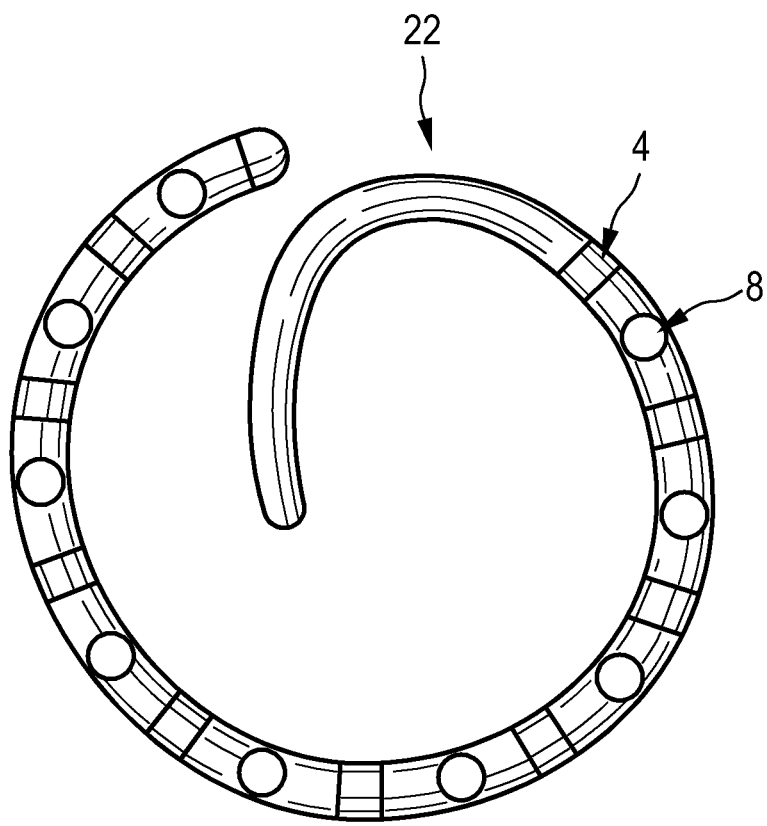
FIG. 2 shows schematically and exemplarily an embodiment of a distal end of a catheter of the energy application apparatus.

FIG. 1 shows schematically and exemplarily an energy application apparatus 1 for applying energy to an object. The energy application apparatus 1 comprises an image providing unit 2 for providing an image of the object 3 being, in this embodiment, a heart of a person 20. The energy application apparatus 1 further comprises a catheter 21 for applying energy to an inner wall of the heart 3. The distal end 22 of the catheter 21 is schematically and exemplarily shown in FIG. 2. The distal end 22 comprises a plurality of energy application elements being ablation electrodes 4 for applying the energy to the wall of the heart 3 at different locations. The ablation electrodes 4 are connected with an energy source 24 via electrical connections for providing electrical energy at the different locations. Preferentially, the energy source 24, the electrical connections and the ablation electrodes 4 are adapted to apply RF energy to the heart 3 at the different locations. The electrical connections are preferentially wires. The ablation electrodes 4, which are not located at the tip of the catheter, are preferentially ring electrodes, and the ablation electrode at the tip of the catheter is preferentially a cap electrode. In other embodiments, the catheter tip may not comprise a cap electrode.

The image providing unit 2 is preferentially adapted to provide an electroanatomic map of the heart 3. In this embodiment, the image providing unit 2 is a storing unit in which the electroanatomic map is stored. The electroanatomic map can be generated by generating a three-dimensional image of the heart 3, for example, by using a computed tomography system, a magnetic resonance imaging system, a nuclear imaging system or an ultrasound imaging system or by impedance, magnetic or electromagnetic-based tracking of the position of the catheter tip, and by measuring the electrical property of the heart at different locations on a wall of the heart, wherein the measured electrical properties are visualized at the respective locations in the three-dimensional image of the heart.

For example, the electroanatomic map can be an activation map reflecting the activation sequence of the anatomical substrate. From this activation map conduction patterns can be derived revealing, for example, zones of late activation or reentrant waves. The information from the activation map can be used to identify ablation targets to which energy should be applied.

The energy application apparatus 1 further comprises a localization unit 6, 7 for localizing the ablation electrodes 4 at the different locations. The localization unit comprises an X-ray fluoroscopy system 6 with an X-ray source 25 and an X-ray detector 26. The X-ray source 25 emits an X-ray beam 27 which traverses the heart 3 including the distal end 22 of the catheter 21. The X-ray beam, which has traversed the heart 3, is detected by the X-ray detector 26. The X-ray detector 26 generates electrical signals depending on the detected X-ray beam and the electrical signals are used by a fluoroscopy control unit 28 for generating an X-ray projection image. The fluoroscopy control unit 28 is also adapted to control the X-ray source 25 and the X-ray detector 26. The X-ray source 25 and the X-ray detector 26 can be adapted to be rotatable around the patient 20 for allowing the X-ray fluoroscopy system 6 to generate X-ray projection images in different directions. The X-ray fluoroscopy system is, for example, a computed tomography fluoroscopy system or a C-arm fluoroscopy system. The X-ray projection images are provided to a position determination unit 7 for determining the position of the ablation electrodes 4 within the heart 3. For determining the position of the ablation electrodes 4 within the heart 3 based on the provided X-ray projection images known position determining methods can be used. For example, the ablation electrodes can be recognized in the different X-ray projection images, which allows the position determination unit to determine the paths of the X-rays which have caused the respective projection of the ablation electrode 4. The position determination unit 7 can be adapted to determine the position of the ablation electrodes 4 within the heart 3 from the intersection of these paths. Or, a three-dimensional image of the ablation electrodes 4 within the heart 3 can be generated from the X-ray projection images, for example, by using a backprojection algorithm, wherein the position determination unit 7 can be adapted to determine the position of the ablation electrodes 4 within the heart 3 by recognizing the ablation electrodes 4 within the heart 3 in the generated three-dimensional image. The position determination unit 7 can also be adapted to determine the orientation of the catheter, in particular, of the ablation electrodes 4.

In other embodiments, the localization unit can comprise other means like a magnetic resonance imaging system or location sensors at the distal end of the catheter for determining the position and optionally also the orientation of the ablation electrodes 4 within the heart 3.

Referring again to FIG. 2, the distal end 22 of the catheter 21 further comprises at least one ultrasound element 18 for generating an ultrasound signal being indicative of a property of the heart 3 at the different locations. In this embodiment, the distal end 22 comprises a plurality of these ultrasound elements 18. The energy application apparatus 1 further comprises a controller 71 for individually controlling the ablation electrodes 4 depending on the local influence of the energy applied by the respective ablation electrode 4. Thus, the controller 71 is adapted such that the influence of energy applied by a respective ablation electrode 4 is locally determined and this determined local influence is used for controlling the respective ablation electrode 4. The controller 71 comprises an energy application influence determination unit 8 and a control unit 9. The energy application influence determining unit 8 is adapted to determine energy application influences of the applied energy to the different locations from the generated ultrasound signals, wherein the generated ultrasound signals are provided to the energy application influence determining unit 8 by an ultrasound control unit 73 which controls the plurality of ultrasound elements 18. The control unit 9 is adapted to individually control a respective ablation electrode 4 depending on the energy application influence determined for the location at which the respective ablation electrode applies energy. In particular, the ablation electrodes 4 and the control unit 9 are adapted to individually control the ablation electrodes 4 depending on the energy application influence determined for the location at which the respective ablation electrode 4 applies energy. The control unit 9 is adapted to control the time, at which power is applied, the duration of applying power, and/or the level of the applied power, in order to control the application of energy to a respective location, depending on the energy application influence determined for the respective location.

The ablation electrodes 4 are adapted to create a lesion line. The lesion line can be a line having an open or closed shape. For example, the lesion line can be a straight or a circular line. The ablation electrodes can be arranged along an annual ring which can be pressed towards, for example, the ostium of the pulmonary veins, for generating a closed lesion line.

The ablation electrodes 4 do not only influence the heart tissue at the respective contact locations, but also between the contact locations. Thus, also at locations at which the ultrasound elements 18 are arranged, the cardiac tissue is influenced by applying the energy. Since the ultrasound elements 18 and the ablation electrodes 4 are arranged alternately, a location, at which an ultrasound element 18 generates an ultrasound signal, is preferentially influenced at least by the two neighbored ablation electrodes 4. Thus, the control unit 9 can therefore be adapted to control an ablation electrode 4 depending on the energy application influences determined from ultrasound signals of ultrasound elements 18 being adjacent to the ablation electrode 4. Neighbored ultrasound elements 18 can therefore be assigned to an ablation electrode 4, wherein the ablation electrode 4 is controlled depending on the energy application influences determined from the ultrasound signals of the assigned ultrasound elements 18.

In another embodiment, several energy application elements, for example, a pair of energy application elements, can be assigned to the same ultrasound element, wherein the control unit is adapted to control the several energy application elements depending on the energy application influence determined from the ultrasound signal of the same ultrasound element.

The energy application influence determining unit 8 is adapted to determine an ablation depth as the energy application influence from the ultrasound signal. In particular, the energy application elements 4 are individually controlled depending on the development of a lesion, which is defined by the ablation depth and caused by the respective energy application element 4. Thus, a local lesion progression is determined and an energy application element 4 is controlled based on the determined local lesion progression.

The energy application apparatus 1 further comprises an object wall thickness determining unit 15 for determining an object wall thickness at the location at which one or several energy application elements 4 apply energy from the ultrasound signal, wherein the control unit 9 is adapted to control the one or several energy application elements 4, e.g. the one or more ablation electrodes 4, depending on the determined local object wall thickness. In particular, ablation electrodes 4 can be individually controlled depending on the development of a lesion caused by one or several ablation electrodes 4 and on the local object wall thickness.

The determination of an ablation depth and the object wall thickness from an ultrasound signal provided by the sensing unit 18 is in the following exemplarily described.

Figure 3:
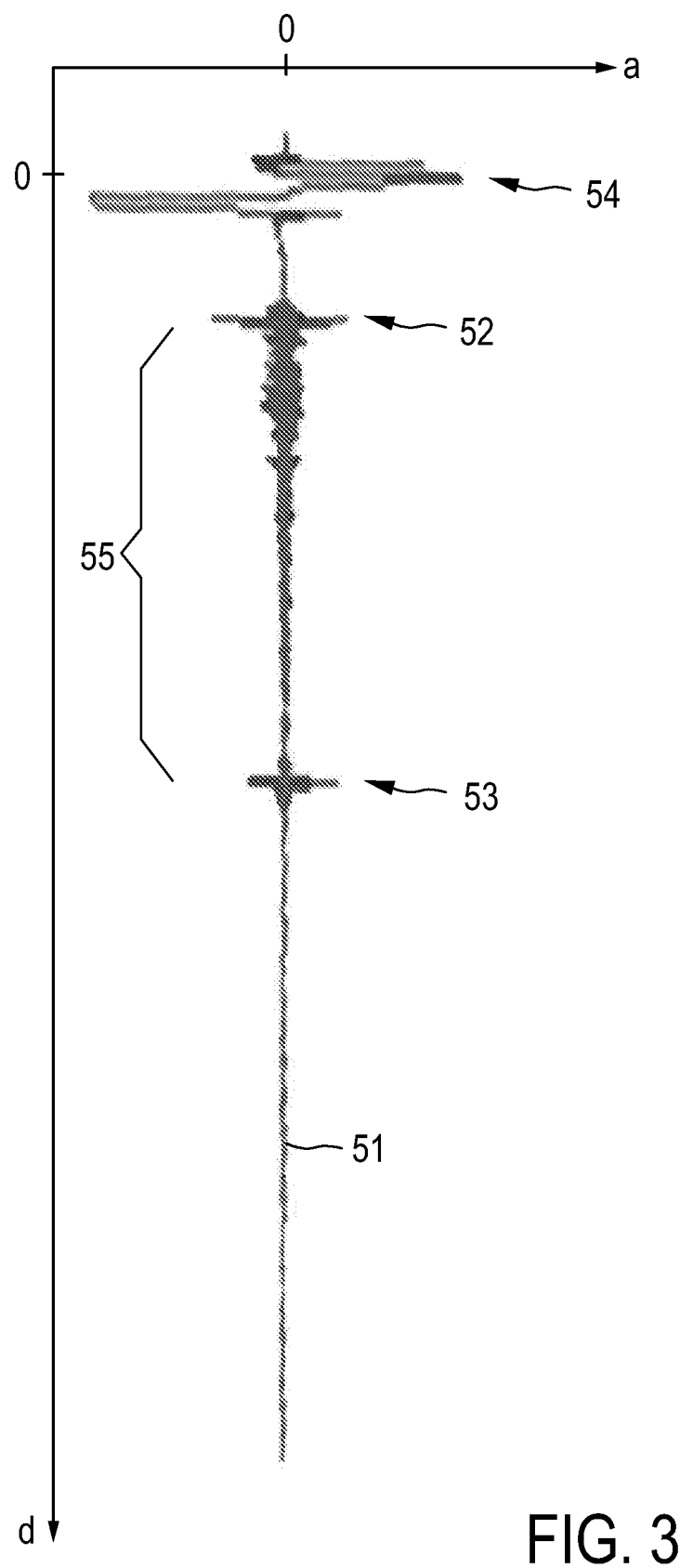
FIG. 3 shows schematically and exemplarily a representation of an echo series produced by reflections of an ultrasound pulse at heart wall tissue.

If an ultrasound pulse is sent out to the object, the ultrasound pulse is reflected at different depths such that echo signals are received by the respective ultrasound element. The echo signals, which are generated by reflection of the ultrasound pulse at different depths within the object, form an echo series. An echo series 51 is schematically and exemplarily shown in FIG. 3. By considering the speed of sound and the time, at which an echo is recorded after the ultrasound pulse has been sent out to the object, the echo series can be translated into a dependence of an ultrasound reflection property of the object on the depths within the object. In FIG. 3, the amplitude a of the echo series in arbitrary units, which corresponds to the ultrasound reflection property, is shown depending on the depth d in arbitrary units that corresponds to the time, at which the respective echo has been received after the pulse has been sent out into the object.

In this embodiment, the object is a heart, wherein the ultrasound pulse is sent out into the heart tissue of the wall. In FIG. 3, the regions of the echo series 51 denoted by 52 and 53, correspond to front and back surfaces of the heart wall. The region 54 is directly generated by the ultrasound pulse. Thus, in a strict sense, the echo series is the graph shown in FIG. 3 without region 54.

The echo series 51 shown in FIG. 3 allows determining the position of the front and back surfaces 52, 53 with respect to the position of an ultrasound element that emits the ultrasound pulse and receives the echoes. The first measured amplitude in the region 54 marks the position of the ultrasound element. Region 54 is followed by a region comprising an amplitude being substantially zero and after a while the amplitude increases again in region 52 marking the first reflection at the object, i.e. marking the front surface of the object. A region 55 comprising smaller amplitudes that correspond to reflections within the tissue of the heart wall follows, and then in the region 53 the amplitude increases again significantly thereby marking the back surface of the heart wall. Thus, the echo series 51 allows determining the positions of the front and back surfaces based on the regions 52 and 53 and, thus, determining the local object wall thickness as the difference between the positions of the front and back surfaces. The region 55 in between is used for determining the ablation depth as will be explained further below.

The position of the increasing amplitude in region 52 after a region comprising an amplitude value being substantially zero can be determined as the position of the front surface of the object. Then, the amplitude substantially decreases in region 55 and the position of the next significant increase of the amplitude (region 53) is determined as the position of the back surface of the heart wall. In other words, after the ring down of the ultrasound element in region 54 a "quiet period" ensues. This quiet period is subsequently terminated by a reflection in region 52 that is associated to the front surface. After this reflection in the region 52 a period 55 occurs that is marked by fast and small temperature changes in the ultrasound intensity. In particular, the envelope of the signal in the period 55 tends to have an exponential decrease in intensity. At the end of the period 55 again a strong reflection is observed in the region 53 that is associated to the back surface. Threshold values can be predefined, in particular relative threshold values can be predefined, wherein the front surface is detected, if a reflection after the "quiet period" exceeds the respective predefined threshold and wherein the back surface is detected, if at the end of period 55 the signal exceeds the respective threshold. The thresholds can be predefined by calibration measurements with walls having known front surface and back surface positions.

The echo series 51 exemplarily shown in FIG. 3 has been generated by an ultrasound pulse that was sent out into the object at a certain time. Several of these ultrasound pulses are sent out to the object at different times, thereby generating echo series at different times. These echo series, which are obtained from different ultrasound pulses at different times, and, thus, which belong to different times, form dynamic echo series. The ultrasound signal which depends on the received dynamic echo series represents therefore the ultrasound reflection properties of the object at different depths and at different times. Such an ultrasound signal is schematically and exemplarily shown in FIG. 4.

Figure 4:
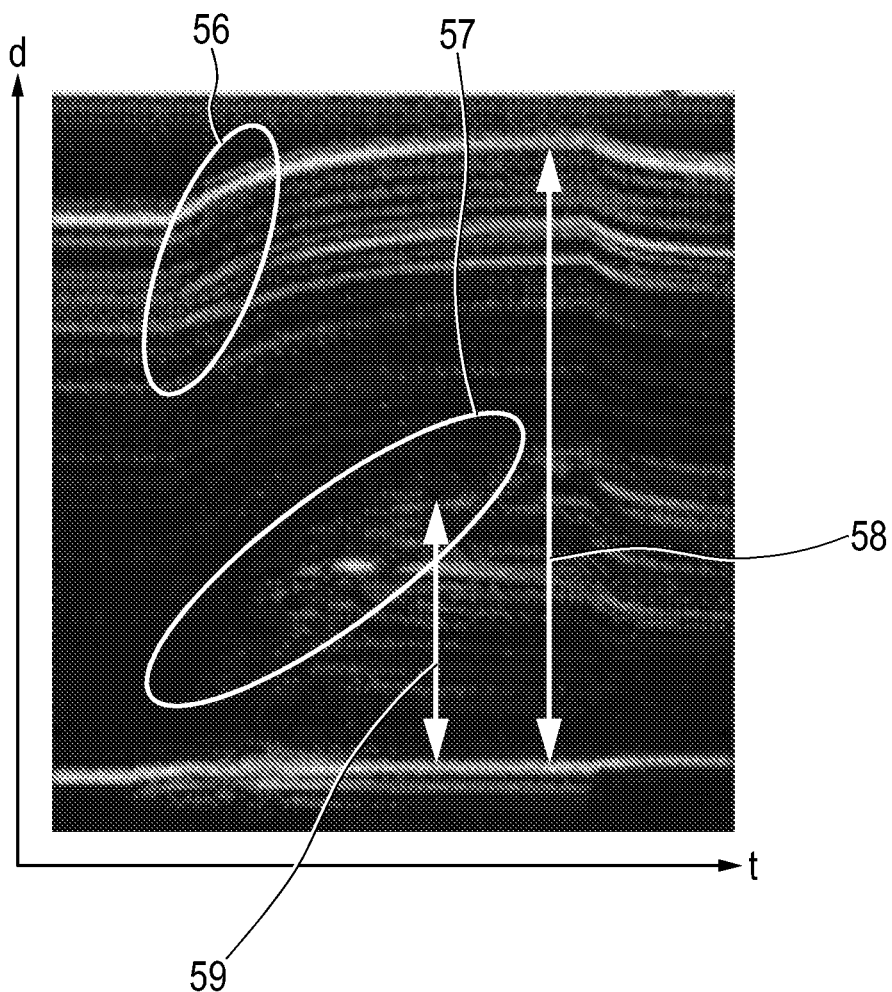
FIG. 4 shows schematically and exemplarily a two-dimensional representation of an ultrasound signal generated by an ultrasound element of the energy application apparatus.

In FIG. 4, different amplitudes of the ultrasound signal are indicated by different brightness, wherein a higher brightness corresponds to larger amplitude. The amplitude is shown depending on the depth d and the time t at which the respective echo series has been generated. The ultrasound signal shown in FIG. 4 forms an image that can be regarded as M-mode image.

By performing an ablation procedure, a lesion is generated in the heart wall, wherein the ablation depth is defined by the boundary of the lesion within the heart wall tissue. The energy application influence determining unit is adapted to determine discontinuities in the ultrasound signal and to determine the ablation depth as a depth of the ultrasound signal at which the discontinuities occur. For example, in FIG. 4 in the first ellipse 56 only continuous variations of the ultrasound signal are present indicating a macroscopic tissue expansion of the heart wall tissue during applying ablation energy to the tissue. In the second ellipse 57 discontinuities in the variation of the ultrasound signal can be observed that indicate the ablation depth. Thus, FIG. 4 shows the progression of the lesion, i.e. the increasing ablation depth, in the second ellipse 57. Based on the observed discontinuities the ablation depth is determined as indicated exemplarily for a certain time by the second double arrow 59, whereas the first double arrow 58 indicates the thickness of the heart wall for a certain time. It should be noted that also the thickness of the heart wall changes with time during performing an ablation procedure due to a macroscopic tissue expansion as can be seen in FIG. 4.

For determining the ablation depth the energy application influence determining unit can be adapted to estimate time-resolved shifts, in particular, macroscopic shifts, in the ultrasound signal due to tissue expansion. In particular, the continuous variations of the ultrasound signal are detected and used for determining the shifts in the ultrasound signal due to tissue expansion for each time for which an ultrasound pulse has been sent out into the object and reflected by the object at different depths. Then, the energy application influence determining unit calculates a shift-compensated ultrasound signal to correct for the shift caused by tissue expansion during ablation. In particular, for different times the amplitude values shown in, for example, FIG. 4 are moved vertically in correspondence with the determined shift for compensating this shift caused by tissue expansion. Then, preferentially the energy application influence determining unit suppresses noise in the shift-compensated ultrasound signal using, for example, a Gaussian filter with, for example, $\sigma=25$. In an embodiment, the energy application influence determining unit is adapted to follow lines corresponding to a constant depth in the shift-compensated ultrasound signal with time, i.e. to follow horizontal lines in a representation of the shift-compensated ultrasound signal that corresponds to the representation shown in FIG. 4, until a disjunctive event occurs. The length of the horizontal lines before this disjunctive event occurs is determined by means of correlation statistics. Then, the energy application influence determining unit is adapted to assign ablated/non-ablated regions based on the determined lengths of connected stretches with a cut-off parameter that remains flexible. The cut-off parameter is, for example, 0.25 s. In particular, in a shift-compensated ultrasound image temporally adjacent pixels on a horizontal line are compared. If along a horizontal line a lesion boundary is not present, the pixels along the horizontal line tend to have roughly the same intensity and only slow variations may occur. In contrast, if a lesion boundary, i.e. the ablation lesion, reaches the horizontal line, the intensity of the pixels in this line change significantly. The depth associated with this significant change in the intensity defines the ablation depth. Preferentially, the energy application influence determining unit is adapted to determine stretches along a horizontal line comprising pixel values having substantially the same intensity. When an ablation front reaches a certain horizontal line, a significant decrease in the length of the stretches in this horizontal line is observed. If the length of the stretches is below a predefined threshold, the energy application influence determining unit determines the ablation depth as the depth associated to the location at which the length of the stretches is below this predefined threshold. This predefined threshold can be determined by calibration measurements, wherein ultrasound signals are generated by sending ultrasound pulses into the object having a known ablation depth. Also the similarity measure for determining whether adjacent pixel intensity values on a horizontal line are similar or not, i.e. whether two adjacent pixel value intensities on a horizontal line belong to the same stretch, can be determined by this calibration. For example, by calibration a relative threshold can be defined indicating the maximum relative difference in the pixel value intensities leading to the decision that these pixel value intensity values are regarded as being similar, i.e. two pixel value intensities are regarded as being similar if their relative difference is equal to or smaller than the maximum relative difference that is preferentially determined by calibration. In an embodiment, stretches having a length larger than 0.25 s, further preferred larger than 0.5 s and even further preferred larger than 1 s, are regarded as indicating that the ablation has not yet occurred at the depth corresponding to the respective horizontal line.

In a further embodiment, the energy application influence determining unit is adapted to Fourier transform the shift-compensated ultrasound signal in which noise has been preferentially suppressed by using, for example, a Gaussian filter. The depth dimension is subdivided into different depth regions, wherein for each depth region each line of signal values defined by the same time is cross correlated with its temporally preceding line of signal values which belong to the same preceding time. Thus, for the respective depth region a number of cross correlation lines is determined. The subdivision of the depth dimension in different depth regions corresponds to a sub division in a vertical direction in the M-mode image shown, for example, in FIG. 4. For example, the vertical lines can be subdivided into about 1000 depth regions. The number of depth regions can be predefined or can be selected automatically or by a user, for example, depending on the thickness of tissue to be examined or the ultrasound frequency. Preferentially, for very thin arterial tissue having a sub-millimeter thickness the number of depth regions is smaller than 1000 and for very thick ventricular tissue having a thickness being larger than 20 mm the number of depth regions is larger than 1000.

The cross correlation lines of the respective depth region are averaged. This averaging is preferentially performed by applying an average filter to the cross correlation lines of the respective depth region. The average filter has, for example, a filter width of eleven lines. However, the average filter can also have a wider or narrower filter width. Moreover, in this embodiment, the energy application influence determining unit is adapted to apply an inverse Fourier transformation on the averaged cross correlation lines of the different depth regions and to determine peaks within the depth regions of the inversely Fourier transformed cross correlation lines. Thus, preferentially, for each depth region and for each time a peak of the cross correlation line is determined.

The energy application influence determining unit can be adapted to determine the depth position of the peak within the respective depth region by cutting the peak out of the respective cross correlation line and by fitting a parabola to the cut out peak. The maximum of the fitted parabola defines the depth position of the peak within the respective depth region at the respective time.

The energy application influence determining unit can further be adapted to determine for each depth region and for each time a shift value from the depth position of the peak within the respective depth region at the respective time. Since the peak is a peak of a cross correlation line, the depth position of the peak within the respective depth region is indicative of the shift between the two lines of signal values within the depth region, which have been cross correlated for determining the respective cross correlation line. The energy application influence determining unit can be adapted to determine the depth position of the peak within the respective depth region as the shift value or the energy application influence determining unit can be adapted to perform further steps for determining a shift value depending on the respective depth position of the peak within the respective depth region. For example, predefined assignments between depth positions of the peak within a depth region and shift values can be stored in the energy application influence determining unit and used for determining a shift value depending on the determined depth position of the respective peak within the respective depth region. These assignments can be determined, for example, by calibration.

The energy application influence determining unit can be adapted to determine an ablation depth and an ablation time depending on the shift values which have been determined for different depth regions and at the different times. For determining the ablation depth and the ablation time a thresholding is preferentially performed on the determined shift values. If a shift value is larger than a predefined shift threshold, the corresponding depth region and time are regarded as an ablation depth, at which the ablation process occurs, and as ablation time, respectively. This shift threshold is predefined and stored in the energy application influence determining unit and can be determined by calibration measurements.

Preferentially, the energy application influence determining unit is adapted to apply a noise reduction filter being a high-frequency filter on the ultrasound signal. For example, the high-frequency filter can be a Hilbert filter. However, the high-frequency filter can also be another filter like a filter using a band pass cut-off frequency or a filter using envelope detection. FIG. 4 shows an ultrasound signal on which a Hilbert filter has been applied.

For interpreting the ultrasound signal shown in FIG. 4, the graph can be interrupted into various parts and re-plotted as exemplarily shown in FIGS. 5 to 9.

In FIGS. 4 to 10 the ultrasound signal for a constant time, i.e. the ultrasound signal along a vertical line in these figures, could be regarded as A-line of the ultrasound signal. In FIGS. 4 to 10 the ultrasound signal is shown depending on the depth d within the heart tissue wall and the time t in arbitrary units.

Figures 5, 6, 7:
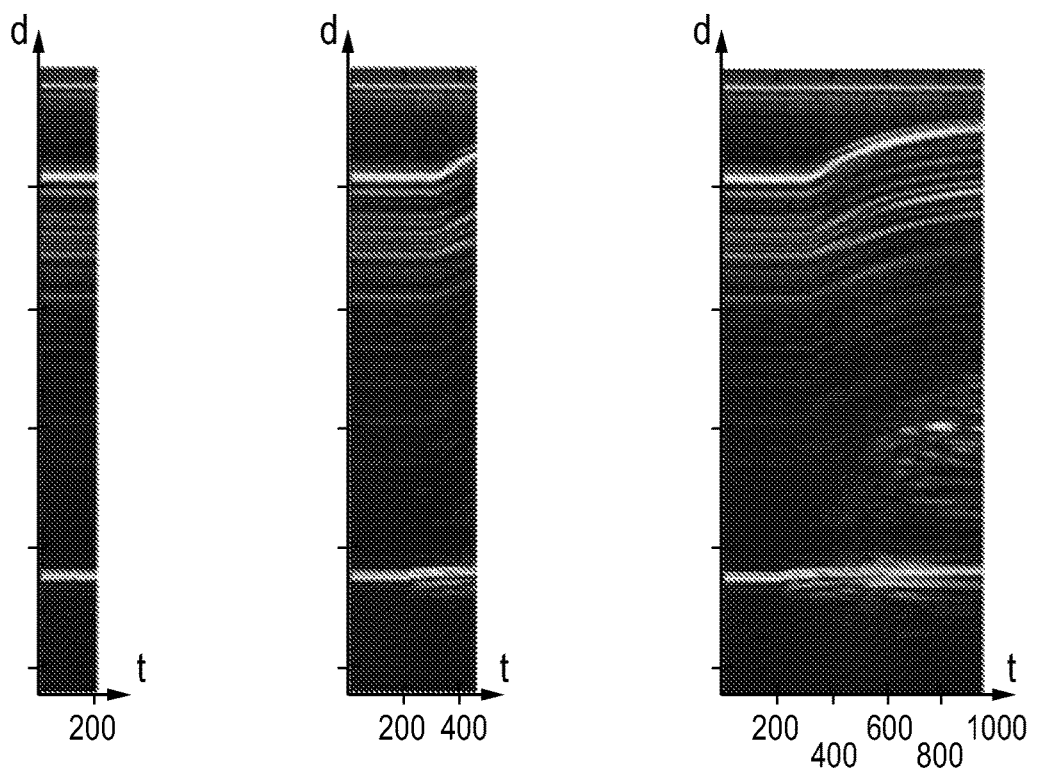
FIGS. 5 to 9 show schematically and exemplarily representations of different parts of an ultrasound signal that correspond to different time periods before, during and after an ablation procedure.

In FIG. 5, the ablation procedure is not applied, for example, a radio frequency ablation electrode 4 is not operated. Thus, the ultrasound signal is constant with respect to variations in time, i.e. the reflection properties of the tissue of the heart wall are substantially not modified.

Figures 8, 9:
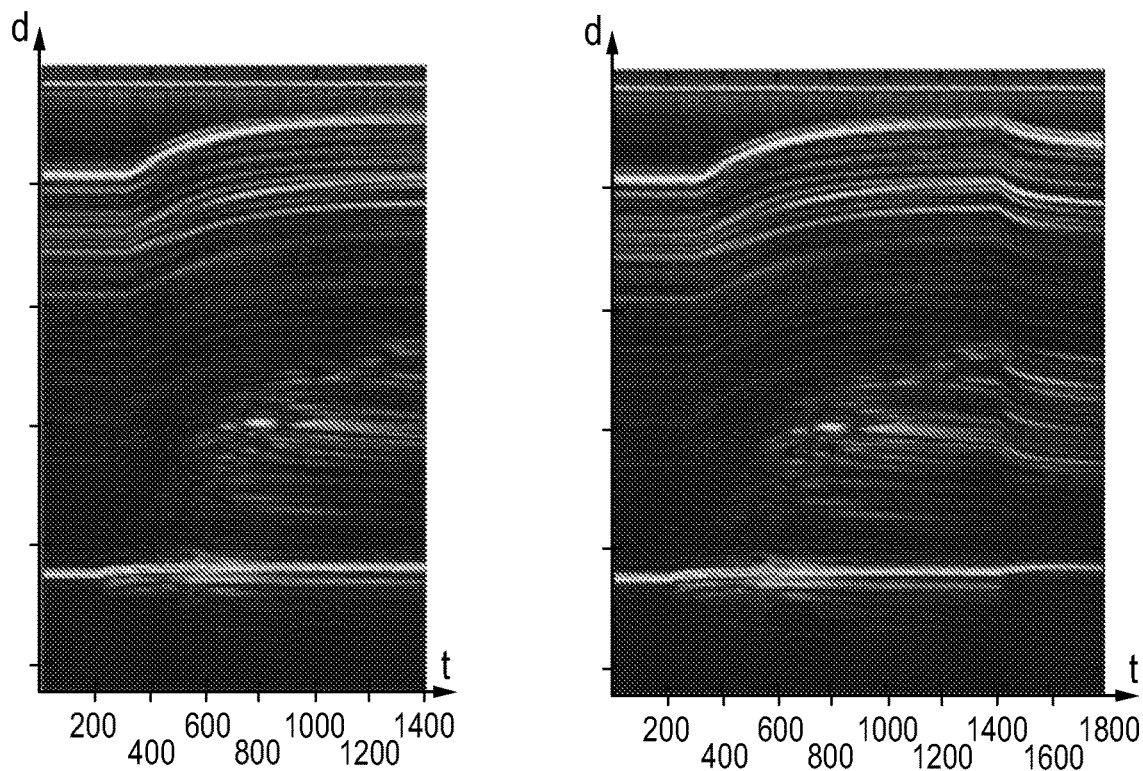

Upon ablation, the part of the tissue to which energy is applied heats up and the ultrasound signal originating from that region starts to change (FIG. 6). It can also be observed that the heated region expands due to the thermal load and pushes the yet not heated part of the tissue in a direction that corresponds to a direction from the bottom to the top in FIGS. 4 to 9. In FIGS. 7 and 8 it is shown how the ultrasound signal changes if the ablation procedure continues. In FIG. 9, the ablation procedure has been stopped, i.e. the heat source (ablation element) has been switched off, resulting in shrinkage by cooling down and a shift of the stripes that correspond to the back surface of the heart tissue wall back towards the original position before ablation. The part of the tissue which was not treated and where no dynamical signal changes are observed preserves its thickness and just shifts its position.

Figure 10:
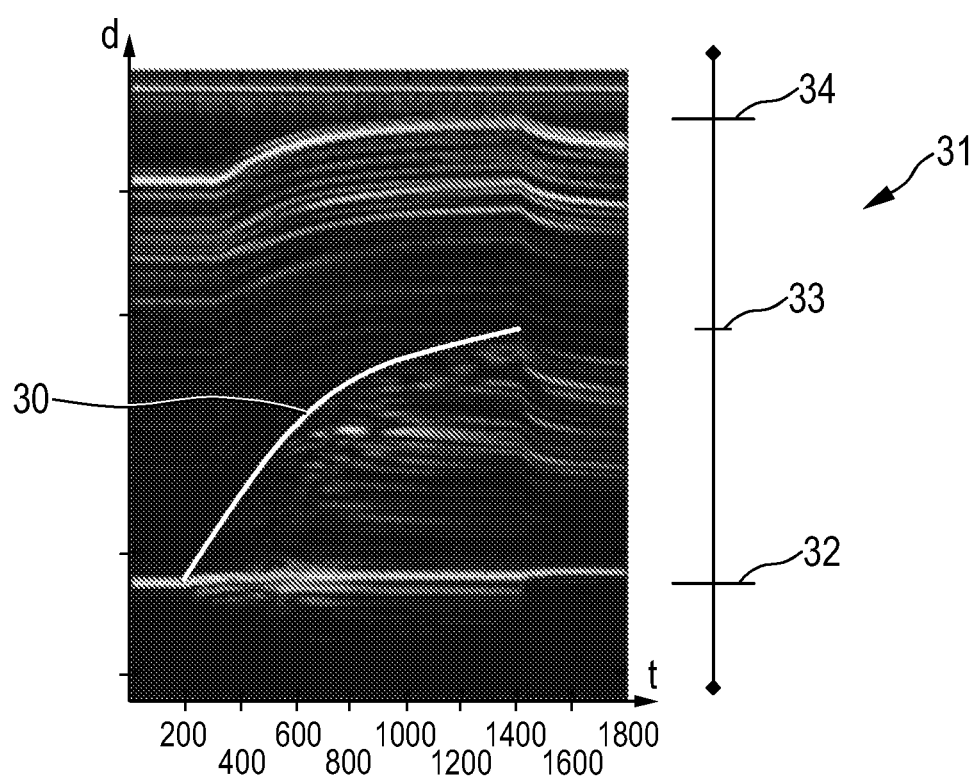
FIG. 10 shows schematically and exemplarily a determined ablation depth and a two-dimensional representation of the ultrasound signal.

FIG. 10 shows schematically and exemplarily a line 30 indicating the ablation depth determined by the energy application influence determining unit at different times, thereby indicating the progression of ablation. FIG. 10 further shows a slide bar 31 indicating the positions of the front surface and the back surface of the heart tissue wall by lines 32 and 34, respectively, and the ablation depth by line 33 for a certain time. In FIG. 10, the slide bar 31 is shown for the moment when the ablation stops. FIG. 10 can be shown on a display 10 for visualizing the progression in ablation.

The energy application apparatus 1 further comprises a navigation unit 29 for allowing the catheter 21, in particular, the distal end 22 of the catheter 21, to be navigated to a desired location within the object. The navigation unit 29 can be adapted to allow a user to navigate the catheter 21 completely by hand or semi-automatically depending on a determined position and preferentially orientation of the distal end 22. The catheter 21 comprises built-in guiding means (not shown in FIG. 1), which can be controlled by the navigation unit 29. The catheter 21 can, for example, be steered and navigated by the use of steering wires in order to guide the distal end 22 to a desired location within the object.

The ultrasound elements can be single probes which allow visualization in one direction, or they can be probes which allow two-dimensional and/or three-dimensional scanning such as a phased array, a rocker probe, a micro-machined ultrasound transducer (MUT) array, et cetera.

In the embodiment described above with reference to FIG. 2, the ultrasound elements 18 are positioned between the ablation electrodes 4 to measure local tissue characteristics, and the distal end 22 is a distal end of a lasso catheter.

Figure 11:
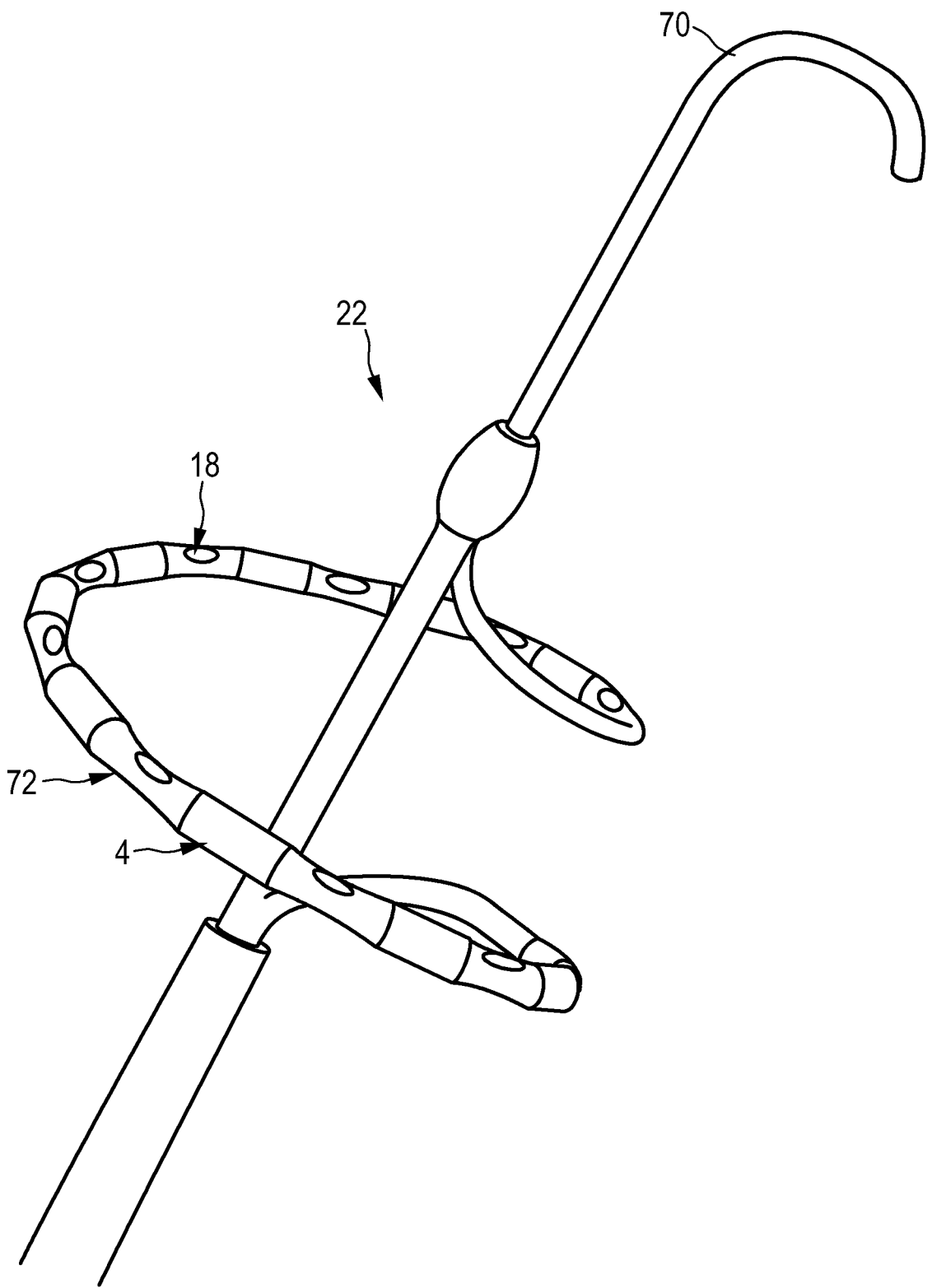
FIGS. 11 to 13 show further embodiments of the distal end of the catheter of the energy application apparatus.

FIG. 11 shows a further embodiment of the distal end 22 of the catheter 21 being a distal end 22 of a catheter which is based on a pulmonary vein ablation catheter (PVAC) from the company Medtronic. In contrast to a standard PVAC, ultrasound elements 18 are positioned between ablation electrodes 4. This embodiment is preferentially used, when the catheter is operated in a bipolar mode. In this embodiment, the distal end 22 has a so-called over-the-wire design, wherein a central wire 70 is adapted to be introduced into a pulmonary vein and, during applying energy, a substantially circular part 72 with the energy application elements 4 and the ultrasound elements 18 sits on the ostium of the pulmonary vein.

Figure 12:
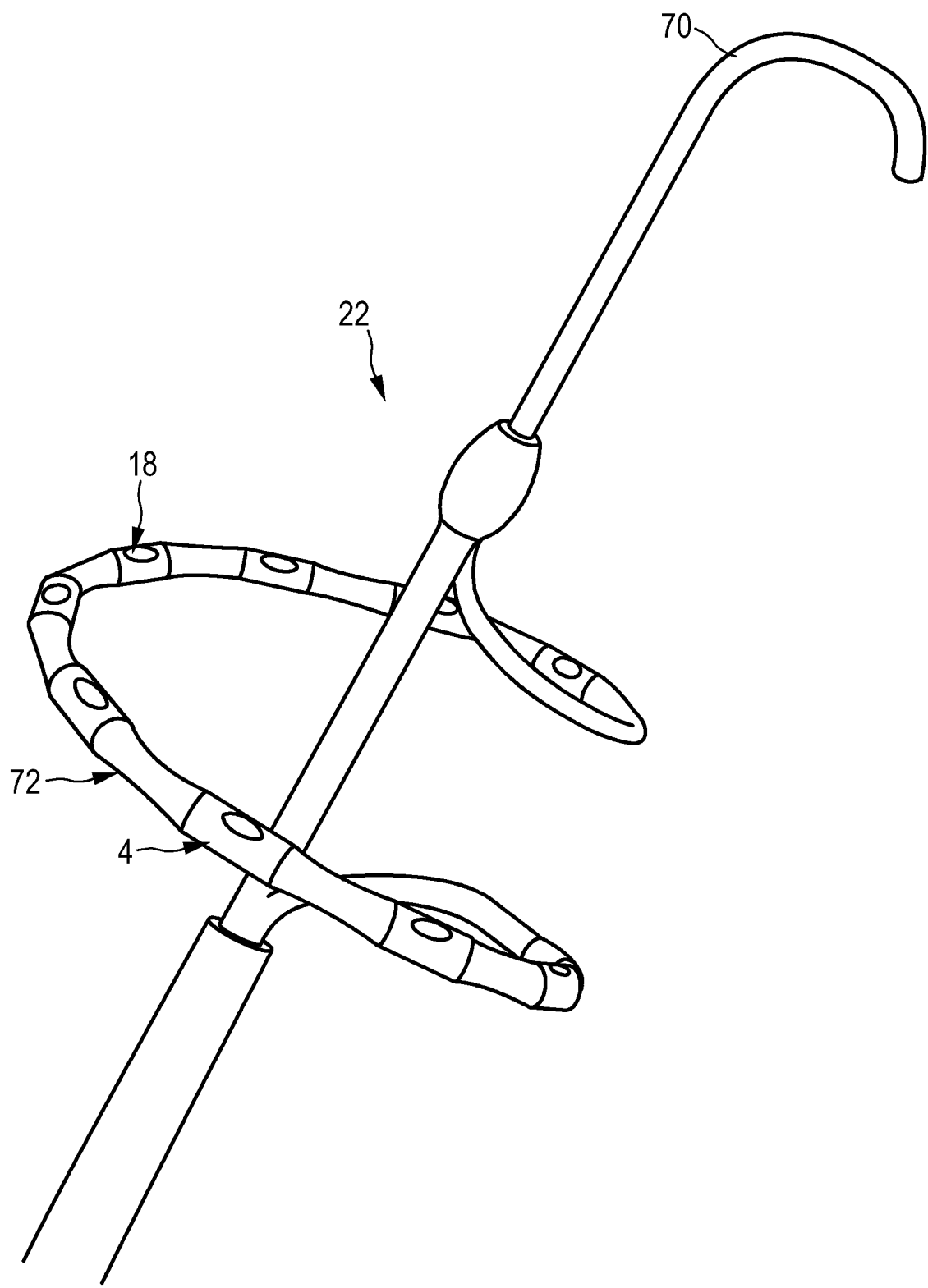

FIG. 12 shows a further embodiment of a distal end 22 of a catheter which is based on a PVAC catheter. In this embodiment, the ablation electrodes 4 and the ultrasound elements 18 are integrated. The ultrasound elements 18 are placed on an outer surface of the ablation electrodes 4. In particular, on the outer surface of each of the ablation electrodes 4 an ultrasound element 18 is placed. This embodiment is preferentially used, when the catheter is operated in a unipolar mode. In a further embodiment, in particular, when the same catheter is designed for use in uni- and bi-polar modes, the ultrasound elements 18 are integrated in the ablation electrodes 4, for example, as shown in FIG. 12, and further ultrasound elements are placed between the ablation electrodes 4 as shown in FIG. 11. Thus, a further embodiment can be regarded as being a combination of the embodiments shown in FIGS. 11 and 12.

Figure 13:
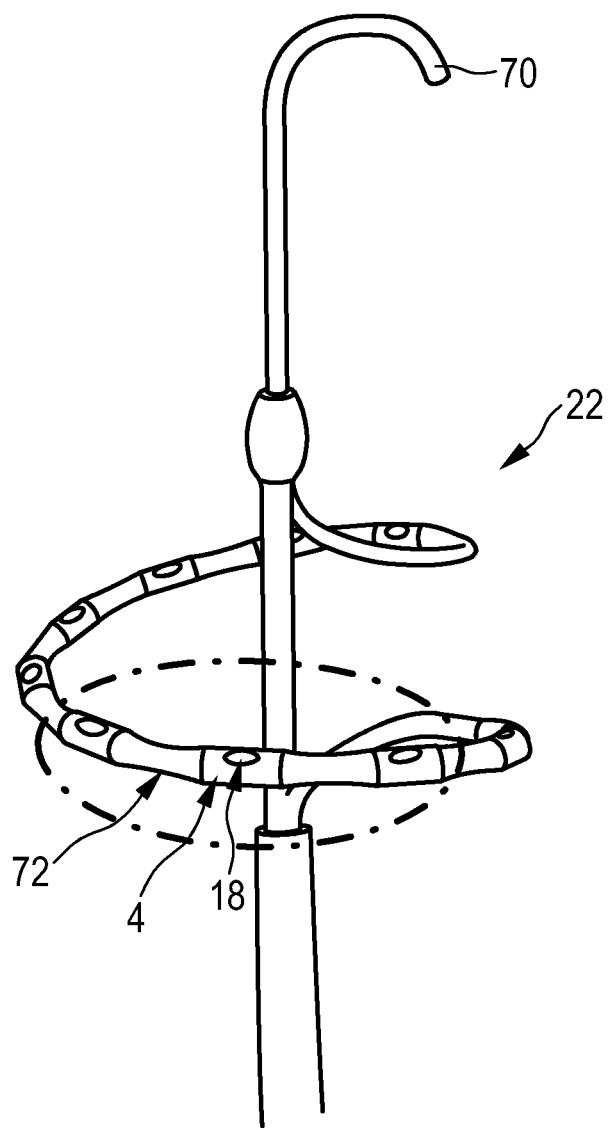
Figure 13:
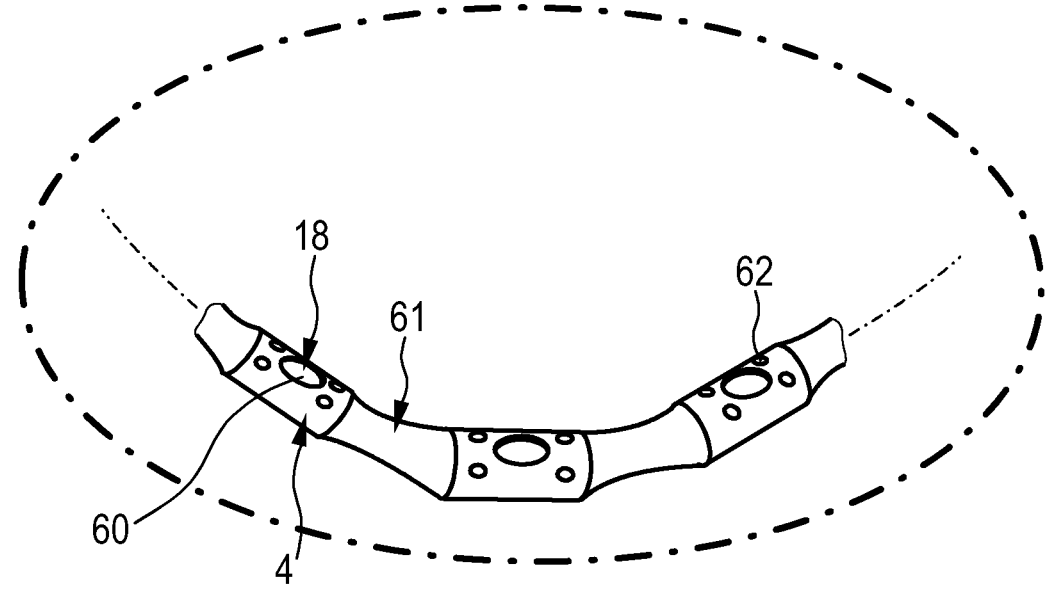

In a further embodiment shown in FIG. 13 the distal end 22 is also a distal end of a catheter which is based on a PVAC catheter. However, in this embodiment irrigation openings 60, 62 are provided in the ablation electrodes 4 for allowing irrigation fluid to leave the catheter. The ultrasound elements 18 are arranged within the distal end 22 of the catheter 21, in particular, within the ablation electrodes 4, such that the property of the cardiac tissue is sensible through the irrigation openings 60. In this embodiment, smaller irrigation openings 62 are used for irrigation purposes only and larger irrigation openings 60 are used for irrigation purposes and for sensing the property of the cardiac tissue through the irrigation openings 60. In a further embodiment, the distal end 22 of the catheter 21 does not comprise the larger irrigation openings 60, but only the smaller irrigation openings 62 and the ultrasound elements 18 are located on the outer surface of the ablation electrodes 4. Thus, the ablation electrodes 4 can comprise irrigation openings, wherein a) the ultrasound elements 18 can be located within the ablation electrodes 4, wherein then the cardiac tissue is preferentially sensed through at least one irrigation opening, or b) the ultrasound elements 18 can be arranged on an outer surface of the ablation electrodes 4. Moreover, in a further embodiment the small irrigation openings 62 may not be present.

The ablation electrodes 4 are connected by a tube material 61, wherein the tube materials 61 includes, for example, electrical wires for controlling the ablation electrodes 4 and the ultrasound elements 18 and can be adapted to allow irrigation fluid to flow through the catheter and to leave the catheter through the irrigation openings.

The energy application apparatus 1 can further comprise an irrigation control unit 63 being connected with the irrigation openings via an irrigation tube, in order to allow a user to control the irrigation of the cardiac tissue.

If an ultrasound element is located within an ablation electrode, the ultrasound element and the ablation electrode are preferentially arranged such that the object can be sensed through an opening of the ablation electrode, wherein, in the above described embodiment, the opening is an irrigation opening. However, this opening can also be an opening which is not used for irrigation purposes, wherein the opening can be closed by a window.

The contact between the ultrasound element and the tissue can be mediated either by the irrigation fluid, in particular, if the space within the ablation electrode is fluidly connected to an irrigation tube, or by an acoustically transparent material like polymethylpentene or parylene, wherein this material can form a window for the opening through which the object is sensed. If the ultrasound elements are integrated into the catheter, in particular, in the PVAC based catheter or lasso catheter, preferentially the ultrasound elements always look in the direction of applying energy to the object. It may therefore not be necessary to change the direction of an ultrasound beam.

Figure 14:
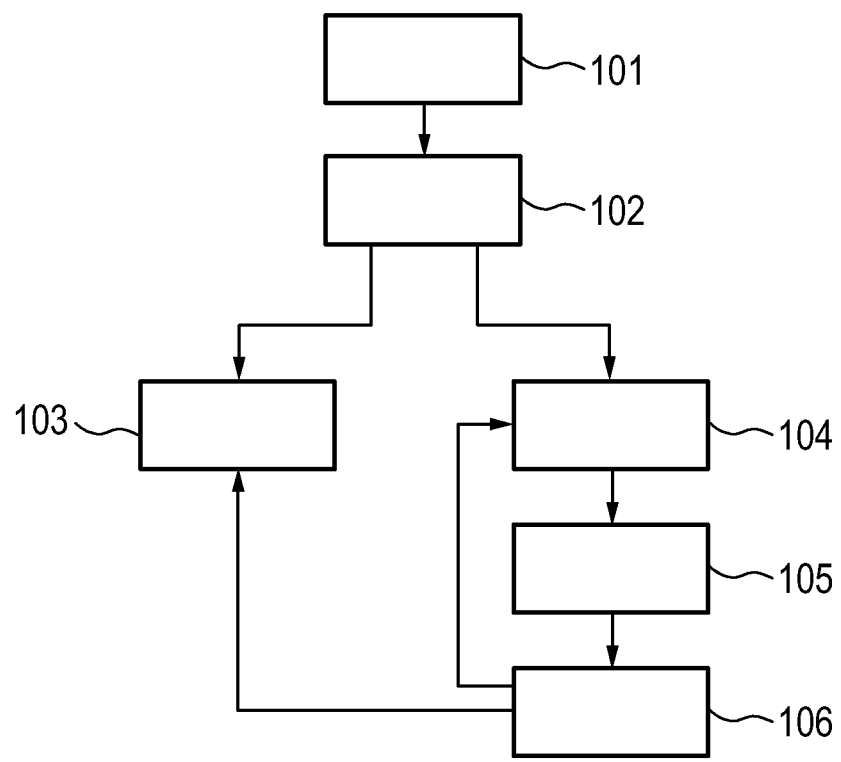
FIG. 14 shows a flowchart exemplarily illustrating an embodiment of an energy application method for applying energy to an object.

In the following an embodiment of an energy application method for applying energy to an object will exemplarily be described with reference to flowchart shown in FIG. 14.

In step 101, an image of the object which is, in this embodiment, a heart 3 of person 20 is provided by the image providing unit 2. In step 102, the energy application elements being preferentially ablation electrodes 4 at the distal end 22 of the catheter 21 are localized for determining locations of the ablation electrodes 4 by the localizing unit 6, 7. The determined locations are preferentially shown on the display 10 with respect to the object 3. The ablation electrodes 4 have preferentially already been navigated to the locations at which energy should be applied to the object. However, if the determined locations of the ablation electrodes 4 do not correspond to desired ablation sites, the ablation electrodes 4 can be navigated to the desired ablation sites by using the navigation unit 29. During this navigation procedure and/or after the navigation procedure has been completed, the location of the ablation electrodes 4 can be determined, in order to assist the user while navigating the ablation electrodes to the desired ablation sites and/or to verify whether the ablation electrodes 4 have been navigated to the desired ablation sites. If the determined locations coincide with the desired ablation sites, in step 103 energy is applied to the object at the different locations by using the ablation electrodes 4.

During applying energy to the object, the ultrasound elements 18 generate ultrasound signals being indicative of a property of the cardiac tissue at the different locations, in step 104. In step 105, an energy application influence of the applied energy to the different locations is determined from the generated ultrasound signals by the energy application influence determining unit 8, and the respective local object wall thickness is determined by the object wall thickness determining unit 15 from the ultrasound signals. In this embodiment, the determined energy application influence is the local ablation depth. In step 106, each energy application element is individually controlled depending on the ablation depth and the local object wall thickness determined for the location at which the respective ablation electrode applies energy by the control unit 9.

The application of energy to the object is preferentially controlled such that the application of energy via a certain energy application element stops, if the lesion created by the certain energy application element has become transmural, i.e. if the local ablation depth corresponds to the local object wall thickness. Since preferentially all energy application elements are controlled individually, it can be ensured that at each location, at which energy is applied, the object, in particular, the heart tissue, is not overtreated or undertreated.

Step 103 on the one side and steps 104, 105, 106 on the other side are preferentially performed simultaneously and repeatedly such that the energy application elements can be locally controlled in real-time depending on the actual ablation depth and local object wall thickness. In an embodiment, the energy application step 103 is performed firstly, after steps 104 and 105 have been performed for at least one time, in order to allow controlling the application of energy depending on the ablation depth and the object wall thickness right from the beginning of the ablation procedure.

Before applying energy to the object, it can be verified whether the ablation electrodes are in contact with the object, in particular with the cardiac tissue, wherein the energy is applied to the object only, if the ablation electrodes are in contact with the object. For example, if the ultrasound elements are integrated into the ablation electrodes, it can be verified whether the object is in contact with the respective ablation electrode based on the position of the surface of the object with respect to the ultrasound element, which can be determined from the ultrasound signal, and based on a known spatial relationship between the respective ablation electrode and the respective ultrasound element. This spatial relationship can be known, because it is known at which position and in which orientation the ultrasound element is arranged within or on the ablation electrode or because a part of the ablation electrode is a little bit hanging over the ultrasound element such that a part of the ultrasound waves is reflected by the respective ablation electrode, for example, two to five percent of the ultrasound intensity can be reflected by a part of the ablation electrode. In the latter case, the ablation electrode is visible in the ultrasound signal and the thus known position of the ablation electrode can be used together with the determined position of the surface of the object for determining whether the ablation electrode is in contact with the object or not. It is also possible to determine whether the respective ablation element is in contact with the object depending on the ultrasound pattern of, for example, an A-line or an M-mode image. For example, if the ultrasound signal is not stable, it can be concluded that the contact between the object and the respective ablation electrode is not good enough or that there is no contact at all. In this case, the distal end of the catheter is preferentially forced towards the object for increasing the contact force. If the ultrasound elements are located on an outer surface of the ablation electrodes, the contact can be determined by determining whether the part of the ultrasound signal, which corresponds to the front wall of the object, has reached the ringdown of the ultrasound signal.

The energy application apparatus can therefore further comprise a contact determination unit for determining whether the individual ablation electrode is in contact with the tissue, wherein the control unit is adapted to apply energy to the tissue via the ablation electrodes only if the contact determination unit has determined a contact between the respective ablation electrode and the tissue.

Catheter ablation can be used for treating cardiac arrhythmias. Briefly, during an ablation procedure cardiac tissue that is in contact with the ablation electrodes is exposed to high temperatures, for example, to temperatures being higher than 60° C., such that the cardiac tissue is destroyed and a lesion of non-conducting scar tissue is formed. RF is preferentially used as energy source. However, the energy application elements can also be adapted to apply another kind of energy like optical energy by using lasers, ultrasound energy (HIFU) or coldness (cryoablation). The ablation procedure can aim to destroy pro-arrhythmogenic tissues sites or to create a line of block to prevent an electrical activation from crossing such a line of block. The energy application apparatus comprising the plurality of ablation elements enables the creation of lesions at multiple spots at the same time and/or the formation of closed or open lesion lines, in particular, of linear lesions.

In order to achieve a complete and permanent block of electrical conduction, the lesion formed by ablation preferentially penetrates through the entire wall thickness, i.e. the lesion is preferentially transmural. However, if too much energy is applied, the tissue can be overheated and neighboring organs can be damaged. This can result in major complications such as an esophageal fistula or cardiac tamponade with severe risk for mortality. The energy application apparatus provides therefore preferentially an accurate and preferably real-time feedback on the lesion progression during the ablation procedure.

The energy application apparatus uses ultrasound imaging for the detection of local heart wall thickness and lesion progression for ablation with a multipoint ablation device. Information obtained about the wall thickness and lesion progression is used to tailor the amount of energy, for example, the time, temperature and/or duration, that is delivered at different spots, i.e. at different locations. The energy application apparatus provides therefore local control points for ablation, which makes the ablation procedure safer and more efficient.

In the arrhythmia therapy a major therapy-related risk is attributed to the overheating of the ablation sites. In the case of overheating, either rupturing of the tissue at the treatment site, thereby potentially releasing life-threatening particles into the blood stream, or damage to neighboring organs and tissues is inflicted. In the case that other organs are affected, fistulas can develop and these are often life-threatening, for example, a fistula in the esophagus has a mortality rate of roughly 75%. A second therapy risk is undertreatment. This results in a return of the arrhythmia soon after the patient has recovered from the procedure, leading to a repeat procedure. Besides the costs and risks involved with the procedure, repeat procedures are more difficult of the therapist because of scar tissue remaining from the first treatment. The optimal settings for an ablation procedure can spatially vary largely due to sizeable intra-patient differences of thickness of the local heart wall, perfusion, blood pressure and velocity, heart rhythm, et cetera. The energy application apparatus can cope with these spatial variations, because the individual ablation electrodes can preferentially be controlled separately depending on the local ablation depth development and local heart wall thickness, which are determined from the ultrasound signals. In particular, the energy application apparatus is adapted to determine the wall thickness and lesion progression locally and in the close proximity of the ablation electrodes, to be able to tailor the amount of energy, in particular, RF energy, that is transferred into the tissue. This improves the application of energy to the object and particularly the ablation procedure, not only because, as already mentioned above, the local object wall thickness varies spatially, but also because the contact force between the respective ablation electrode and the tissue strongly influences the energy transfer to the tissue and because the contact force may be different for different ablation electrodes. The energy application apparatus is therefore preferentially adapted to use ultrasound imaging for detection of local heart wall thickness and/or lesion progression simultaneously and at multiple spots for a multipoint ablation device. This feedback is preferentially used for tailored application of energy for ablation while ablating at multiple spots.

In the embodiment described above with reference to FIG. 2 the ultrasound elements are integrated into a lasso catheter, and in the embodiments described above with reference to FIGS. 11 to 13 the ultrasound elements are integrated into a PVAC based catheter. An advantage of this integration is that, when ablating, for example, the pulmonary vein ostia, the ultrasound elements can always be forward looking such that the direction of an ultrasound beam has preferentially not to be changed, i.e. preferentially there is no need to change the ultrasound beam direction, because the ultrasound elements are preferentially integrated with the energy application elements such that they sense the object in the right direction, i.e. at locations adjacent to locations at which energy is applied or directly at the locations at which energy is applied. Also if the ultrasound elements are integrated into other kinds of catheters, they are preferentially arranged together with the energy application elements such that the ultrasound elements can sense the location, at which energy is applied, or an adjacent location, without needing to change the direction of the ultrasound beam used for sensing the respective location.

The ultrasound elements are preferentially ultrasound transducers which are preferentially operated within a frequency range of 15 MHz to 30 MHz. Although in the above described embodiments the ultrasound elements are integrated into a lasso catheter and into a PVAC based catheter, in further embodiments the ultrasound elements can also be integrated into another kind of catheter like a basket or balloon catheter. In particular, the ultrasound elements can also be integrated into other types of catheters having multiple energy application elements like catheters with a changeable distal end, wherein the shape of the distal end can be modified by a user. For example, multi-array ablation catheters (MAAC) or multi-array septal catheters (MASC) from the company Medtronic can be used.

Although in the above mentioned embodiments the object to which energy is applied is a heart of a person, the energy application apparatus can also be adapted to apply energy to a heart of an animal or to apply energy to another organ or another part of a person or an animal. The energy application apparatus can also be adapted to apply energy to a technical object.

Although in the above described embodiments the energy application influence determining unit is adapted to determine an ablation depth as energy application influence, in other embodiments, the energy application influence determining unit can also be adapted to determine another energy application influence. The appropriate kind of energy application influence depends on the kind of energy applied to the object and on the object itself. The energy application influence characterizes a change of the object induced by the application of the energy. If, for example, the density of the object is changed by applying energy to the object, the density of the object at the location at which energy is applied could be regarded as an energy application influence determined by the energy application influence determining unit.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Determinations like the determination of an energy application influence, in particular, of an ablation depth, and the determination of the object wall thickness, performed by one or several units or devices can be performed by any other number of units or devices. The determinations and/or the control of the energy application apparatus in accordance with the energy application method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to an energy application apparatus for applying energy to an object. A plurality of energy application elements applies energy to the object at different locations and at least one ultrasound element generates an ultrasound signal being indicative of a property of the object at the different locations, wherein at least one energy application element is individually controlled depending on an energy application influence, in particular, an ablation depth, determined for the location at which the at least one energy application element applies energy from the ultrasound signal. Thus, at least one local control point for applying energy to the object is provided, thereby improving the control of applying energy to the object.

The invention claimed is:

1. An energy application apparatus for applying energy to an object, the energy application apparatus comprising:
    a plurality of energy application elements for applying ablation energy to the object at different energy application element locations;
    each of the plurality of energy application elements having an integral ultrasound element, the integral ultrasound element generating ultrasound signals being indicative of a property of the object at an energy application element location of the energy application element with which the ultrasound element is integral;
    an energy application influence determining unit for determining an ablation depth at each energy application location based on the generated ultrasound signals; and
    a control unit adapted for individually controlling each respective energy application element based on the ablation depth determined from ultrasound signals of the ultrasound element integral to the respective energy application element.

2. The energy application apparatus as defined in claim 1, wherein the energy application elements are ablation electrodes for creating a lesion line.

3. The energy application apparatus as defined in claim 1, wherein the energy application apparatus comprises a catheter for introducing the plurality of energy application elements and integral ultrasound elements into the object.

4. The energy application apparatus as defined in claim 3, wherein the catheter comprises at least one irrigation opening for allowing irrigation fluid to leave the catheter, wherein the at least one ultrasound element is arranged within the catheter such that the property of the object is sensible through the at least one irrigation opening.

5. The energy application apparatus as defined in claim 1, wherein the ultrasound signal represents ultrasound reflection properties of the object at different depths, wherein the energy application influence determination unit is adapted to determine a discontinuity of the ultrasound signal and to determine the ablation depth as the depth of the ultrasound signal at which the discontinuity occurs.

6. The energy application apparatus as defined in claim 1, wherein the energy application apparatus further comprises an object wall thickness determining unit for determining an object wall thickness at the location at which each energy application element applies energy from the ultrasound signal of the integral ultrasound element, wherein the control unit is adapted to control each energy application element depending on the determined object wall thickness.

7. The energy application apparatus as defined in claim 1, wherein the ultrasound elements are placed on an outer surface of the energy application elements.

8. The energy application apparatus as defined in claim 7, wherein the energy application elements comprise an outer surface with an opening and wherein the ultrasound elements are located within the energy application elements such that the property of the object can be sensed through the opening.

9. The energy application apparatus as defined in claim 1, wherein the energy application influence determining unit is further adapted to estimate a time resolved shift in an ultrasound image from the ultrasound signal due to tissue expansion, calculate a shift-compensated ultrasound signal, and use the shift-compensated ultrasound signal to determine the ablation depth.

10. The energy application apparatus as defined in claim 1, further comprising a catheter comprising a distal end, wherein the distal end comprises a circular portion, wherein the plurality of energy application elements is positioned on the circular portion such that the plurality of energy application elements is arranged in a circular arrangement, and wherein each integral ultrasound element of the plurality of energy application elements is arranged to direct ultrasound energy toward a same surface of the object.

11. A catheter for being introduced into an object, the catheter comprising:
    a plurality of energy application elements for applying ablation energy to the object at different locations;
    each of the plurality of energy application elements having an integral ultrasound element, the integral ultrasound element generating ultrasound signals being indicative of an ablation depth at an energy application element location;
    wherein the catheter is adapted to cooperate with:
    an energy application influence determining unit for determining the ablation depth at each energy application location based on the generated ultrasound signals.

12. A controller for controlling the application of energy to an object, wherein the controller is adapted to cooperate with:
    a plurality of energy application elements for applying ablation energy to the object at different energy application locations; and
    each of the plurality of energy application elements having an integral ultrasound element, the integral ultrasound element generating ultrasound signals being indicative of a property of the object at an energy application element location of the energy application element with which the ultrasound element is integral;
    wherein the controller comprises:
    an energy application influence determining unit for determining an ablation depth at each energy application location based on the generated ultrasound signals; and
    a control unit adapted for individually controlling each respective energy application element based on the ablation depth determined from ultrasound signals of the ultrasound element integral to the respective energy application element.

13. A non-transient computer readable storage medium having encoded thereon a computer executable program for applying energy to an object, the program comprising program code means comprising:
    program code for applying ablation energy to the object at different energy application locations by a plurality of energy application elements;
    program code for generating ultrasound signals being indicative of a property of the object at the energy application locations by ultrasound elements integral with each of the plurality of energy application elements;
    determining an ablation depth at each energy application location based on the generated ultrasound signals by an energy application influence determining unit; and
    individually controlling each respective energy application element by a control unit, wherein the control unit is adapted to control each respective energy application element based on the ablation depth determined from ultrasound signals of the ultrasound element integral to the respective energy application element.

* * * * *